(12) United States Patent
Mechlenburg (10) Patent No.: US 8,746,247 B2
(45) Date of Patent: Jun. 10, 2014

(54) SYSTEM AND METHOD FOR TREATING LUNG DISEASE USING POSITIVE PRESSURE AIRWAY SUPPORT

(75) Inventor: Douglas Mechlenburg, Murrysville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 429 days.

(21) Appl. No.: 13/131,127

(22) PCT Filed: Nov. 21, 2009

(86) PCT No.: PCT/IB2009/055258
§ 371 (c)(1),
(2), (4) Date: May 25, 2011

(87) PCT Pub. No.: WO2010/070497
PCT Pub. Date: Jun. 24, 2010

(65) Prior Publication Data
US 2011/0240025 A1    Oct. 6, 2011

Related U.S. Application Data

(60) Provisional application No. 61/139,064, filed on Dec. 19, 2008.

(51) Int. Cl.
*A61M 11/00*    (2006.01)

(52) U.S. Cl.
USPC ............ 128/204.21; 128/204.18; 128/204.23

(58) Field of Classification Search
USPC ............ 128/204.18, 204.21, 204.23, 204.26, 128/716–719
See application file for complete search history.

(56) References Cited

U.S. PATENT DOCUMENTS

| | | | |
|---|---|---|---|
| 4,533,346 A * | 8/1985 | Cosgrove et al. | 604/66 |
| 5,535,738 A | 7/1996 | Estes et al. | |
| 2003/0029452 A1 * | 2/2003 | Suki et al. | 128/204.18 |
| 2006/0037615 A1 * | 2/2006 | Wilkinson et al. | 128/204.23 |
| 2007/0089745 A1 | 4/2007 | Gabriel et al. | |
| 2008/0257337 A1 | 10/2008 | Denyer et al. | |

FOREIGN PATENT DOCUMENTS

WO    2007134099 A2    11/2007

* cited by examiner

*Primary Examiner* — Steven Douglas
(74) *Attorney, Agent, or Firm* — Timothy A. Nathan (57) ABSTRACT

A method of treating lung disease, such as asthma or COPD, is provided that includes delivering positive pressure support to an airway of a patient during a plurality of respiratory cycles, and automatically varying a pressure level of the positive pressure support during at least a portion of the inspiratory phase of the patient in a number of the respiratory cycles.

18 Claims, 9 Drawing Sheets

SYSTEM AND METHOD FOR TREATING LUNG DISEASE USING POSITIVE PRESSURE AIRWAY SUPPORT

This patent application claims the priority benefit under 35 U.S.C. §119(e) of U.S. Provisional Application No. 60/139,064 filed on Dec. 19, 2008, the contents of which are herein incorporated by reference.

The present invention relates to systems and methods for treating lung diseases such as asthma, COPD or other lung diseases that effect the airways, and in particular to systems and methods for treating such lung diseases using positive pressure airway support.

Asthma is a chronic lung disease that affects a person's bronchial tubes, also known as airways, which are the tubes that carry air into and out of the lungs. People that have asthma have airways that are inflamed as a result of swelling and the production of excess mucus. The airways of people that have asthma are also overly sensitive to things like exercise, dust, or cigarette smoke. This over-sensitivity causes the smooth muscle that surrounds the airways to tighten up when a person with asthma exercises or breathes such substances in. The combination of airway inflammation and muscle tightening narrows the airways and makes it difficult for air to move through them. As a result, people that have asthma experience recurring periods of wheezing, chest tightness, shortness of breath, and coughing, commonly called asthma attacks.

Typically, asthma is treated with medication in either or both of the following two ways. The first way employs what are commonly known as rescue medications. Rescue medications are administered as needed to immediately stop the symptoms of an acute attack. The second way attempts to manage the asthma and prevent attacks from occurring using what are commonly known as controller medications. Such controller medications are typically taken daily regardless of whether an attack has occurred and attempt to treat the airway inflammation associated with asthma.

While the use of medication for the treatment of asthma has proven to be effective in many cases, some people do not completely respond to medication and/or suffer from adverse side effects. In addition, in general, most physicians and/or asthma sufferers prefer to utilize the minimum medication dose required to be effective. Thus, there is always a need for additional therapy methods to be used in conjunction with and/or in place of (at least partially) medication to treat asthma and/or other lung diseases such as COPD that effect the airways.

In another embodiment, a method of treating lung disease, such as asthma or COPD, is provided that includes delivering positive pressure support to an airway of a patient during a plurality of respiratory cycles, and automatically varying a pressure level of the positive pressure support during at least a portion of the inspiratory phase of the patient in a number of the respiratory cycles. The automatically varying of the pressure level may include pseudorandomly varying the pressure level within predetermined limits, or, alternatively, varying the pressure level according to a predetermined scheme. In addition, the method also include automatically varying a second pressure level of the positive pressure support during at least a portion of an expiratory phase of the patient in the number of the respiratory cycles.

In a further alternative embodiment, the invention provides a method of treating lung disease, such as asthma or COPD, that includes delivering bi-level positive pressure support to an airway of a patient during a plurality of respiratory cycles, and automatically varying a differential between an inspiratory positive airway pressure (IPAP) level and an expiratory positive airway pressure (EPAP) level of the bi-level pressure support during a number of the respiratory cycles. In one particular embodiment, the differential is automatically varied by pseudorandomly varying the differential within predetermined limits. In another embodiment, the differential is automatically varied by varying the differential according to a predetermined scheme, such as, without limitation, a predetermined pattern of levels. In another particular embodiment, the bi-level positive pressure support therapy has a predetermined baseline IPAP level and a predetermined baseline EPAP level during an initial number of the respiratory cycles that is different than the number of respiratory cycles during which the differential is automatically varied. The varying of the differential may include varying only the IPAP level, or, alternatively, varying either or both of the IPAP level and the EPAP level.

In another embodiment, the invention provides a pressure support system for treating lung disease, such as asthma or COPD, that includes a pressure generating system, a patient circuit operatively coupled to the pressure generating system, and a controller operatively coupled to the pressure generating system. The controller is adapted to control the pressure generating system to deliver positive pressure support to an airway of a patient through the patient circuit during a plurality of respiratory cycles and automatically vary a pressure level of the positive pressure support during at least a portion of the inspiratory phase of the patient in a number of the respiratory cycles. The controller may be adapted to automatically vary the pressure level pseudorandomly within predetermined limits, or, alternatively, the controller may be adapted to automatically vary the pressure level according to a predetermined scheme. Also, the controller may be further adapted to automatically vary a second pressure level of the positive pressure support during at least a portion of an expiratory phase of the patient in the number of the respiratory cycles.

In yet another embodiment, the invention provides a pressure support system for treating lung disease, such as asthma or COPD, that includes a pressure generating system, a patient circuit operatively coupled to the pressure generating system, and a controller operatively coupled to the pressure generating system. The controller is adapted to control the pressure generating system to deliver bi-level positive pressure support to an airway of a patient through the patient circuit during a plurality of respiratory cycles and automatically vary a differential between an inspiratory positive airway pressure (IPAP) level and an expiratory positive airway pressure (EPAP) level of the bi-level positive pressure support during a number of the respiratory cycles.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

The accompanying drawings illustrate presently preferred embodiments of the invention, and together with the general description given above and the detailed description given below, serve to explain the principles of the invention. As shown throughout the drawings, like reference numerals designate like or corresponding parts.

As employed herein, the statement that two or more parts or components are "coupled" together shall mean that the parts are joined or operate together either directly or through one or more intermediate parts or components.

As employed herein, the term "number" shall mean one or an integer greater than one (i.e., a plurality).

It has been hypothesized that asthma is the result of both a smooth muscle cell chemical deficiency (i.e., p38 MAPK and HSP27 inhibition) and a dynamic smooth muscle dilation deficiency (i.e., loss of mechanical perturbation and unencumbered muscle shortening resulting in excessive restriction of the airways). In plain English, this means that the upper airway in normal people is kept open because their upper airway smooth muscles can both process a key protein that is responsible for lengthening the muscle, and because they mechanically manipulate the airway muscles by more varied breathing patterns (i.e., a normal combination of both deep inspirations and more shallow inspirations). In asthmatic individuals, for some reason the processing of these key proteins is inhibited, which causes their airway muscles to be shorter (more constricted). Asthmatic individuals also do not have the same dynamic range of breathing, probably due to the shorter muscle state just described.

Positive pressure support systems that provide a flow of breathing gas to an airway of a patient at an elevated pressure are well known. One form of such pressure support is known as bi-level positive pressure support therapy. In bi-level positive pressure support therapy, the pressure of gas that is delivered to the patient varies with the patient's breathing cycle. Specifically, an inspiratory positive airway pressure (IPAP) is provided during the inspiratory phase of the patient's breathing cycle, and an expiratory positive airway pressure (EPAP) is provided during the expiratory phase of the patient's breathing cycle. The EPAP is lower than the IPAP so that the patient exhales against a relatively low pressure as compared to the IPAP pressure, thereby increasing the comfort to the patient. The BiPAP® and Bi-Flex® family of pressure support devices manufactured by Respironics, Inc. of Murrysville, Pa., are examples of pressure support devices that provide various forms of bi-level positive pressure support therapy. In addition, several U.S. patents describe bi-level positive pressure support system in detail, including U.S. Pat. Nos. 5,433,193; 5,313,937; 5,239,995; 5,148,802; 6,532,960; and 6,640,806, all of which are hereby expressly incorporated herein by reference as if set forth in their entirety herein.

Figure 1:
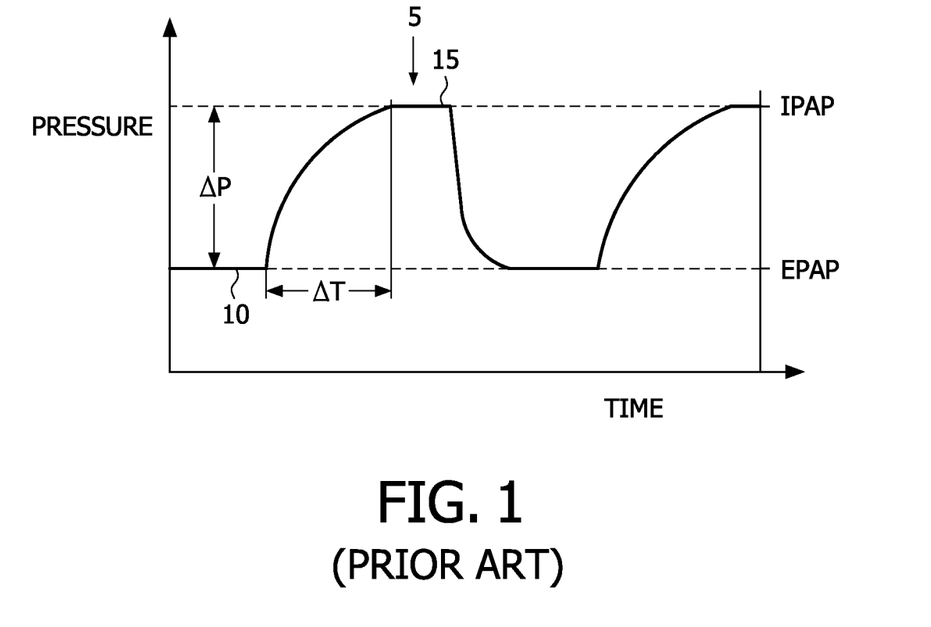
FIG. 1 is a typical prior art pressure curve that is output by a bi-level positive pressure support system.

As discussed above, a bi-level positive pressure support system (as that term is used herein) provides an IPAP level of pressure to the airway of a patient during at least a portion of inhalation and an EPAP level of pressure during at least a portion of exhalation. FIG. 1 schematically depicts a typical pressure curve 5 that is output by an exemplary bi-level positive pressure support system. During an expiratory phase of the patient's breathing cycle, the pressure curve 5 is at the expiratory pressure (EPAP) 10. At the end of exhalation, i.e., at the onset of the subsequent inhalation phase of the patient's breathing cycle, the pressure curve 5 changes to an inspiratory pressure (IPAP) 15. When the system detects the end of inspiration, i.e., at the onset of the subsequent exhalation phase, the pressure curve 5 returns to the lower expiratory pressure (EPAP) 10, and the cycle starts over. The difference in pressure between EPAP 10 and IPAP 15 is designated as ΔP in FIG. 1. As seen in FIG. 1, in the exemplary pressure waveforms shown therein, this pressure change occurs gradually (rather than instantaneously), which helps to improve patent comfort. This gradual transition effect is measured by the time it takes the system pressure to increase from EPAP 10 to IPAP 15 and is referred to as the "rise time" of the bi-level pressure support system. Similarly, rather than an instantaneous transition from IPAP 15 to EPAP 10, FIG. 1 shows a gradual transition of the system pressure from IPAP 15 to EPAP 10. This gradual transition effect is measured by the time it takes the system pressure to decrease from IPAP 15 to EPAP 10 and is referred to as the "fall time" of the bi-level pressure support system. Furthermore, while the transitions from EPAP 10 to IPAP 15 and from IPAP 15 to EPAP 10 are shown as exponential ramps in FIG. 1 (and in FIGS. 4, 6 and 7 described elsewhere herein), that is meant to be exemplary only and it should be understood that the ramping may also be a straight line (fixed rates of transition) or any other transitional waveform (including a square wave) from one generally constant level to another.

As described in greater detail herein, the present invention, in various embodiments, provides for the treatment of lung diseases that effect the airways, such as asthma and COPD, using positive pressure support therapy, preferably bi-level positive pressure support therapy. Specifically, the present invention employs positive pressure support therapy, preferably bi-level positive pressure support therapy, to address the upper airway muscle mechanical perturbation issues and deficiencies common to individuals suffering from lung diseases that effect the airways, such as asthmatic individuals. More specifically, in one embodiment, the present invention treats lung disease, such as asthma or COPD, using positive pressure support therapy, preferably bi-level positive pressure support therapy, by determining a parameter indicative of the patient's pulmonary mechanics, such as, without limitation, upper airway resistance or lung compliance, and then determining and varying the positive pressure support therapy settings (e.g., the pressure level during at least a portion of the inspiratory phase or the IPAP and EPAP settings) based on the determined parameter. In another embodiment, the present invention treats lung disease, such as asthma or COPD, using positive pressure support therapy, preferably bi-level positive pressure support therapy, by dynamically and preferably pseudorandomly varying the positive pressure support therapy settings (such as the pressure level during at least a portion of the inspiratory phase or the range of the IPAP and EPAP settings) employed during the positive pressure support therapy session. The positive pressure support therapy methods described herein are preferably intended to be used by an individual regularly, such as, without limitation, one or more times each day, to treat the individual's condition, regardless of whether the individual is currently suffering any acute symptoms. One goal or objective of the therapy is to diminish the individual's need for controller and/or rescue medications.

Figure 2:
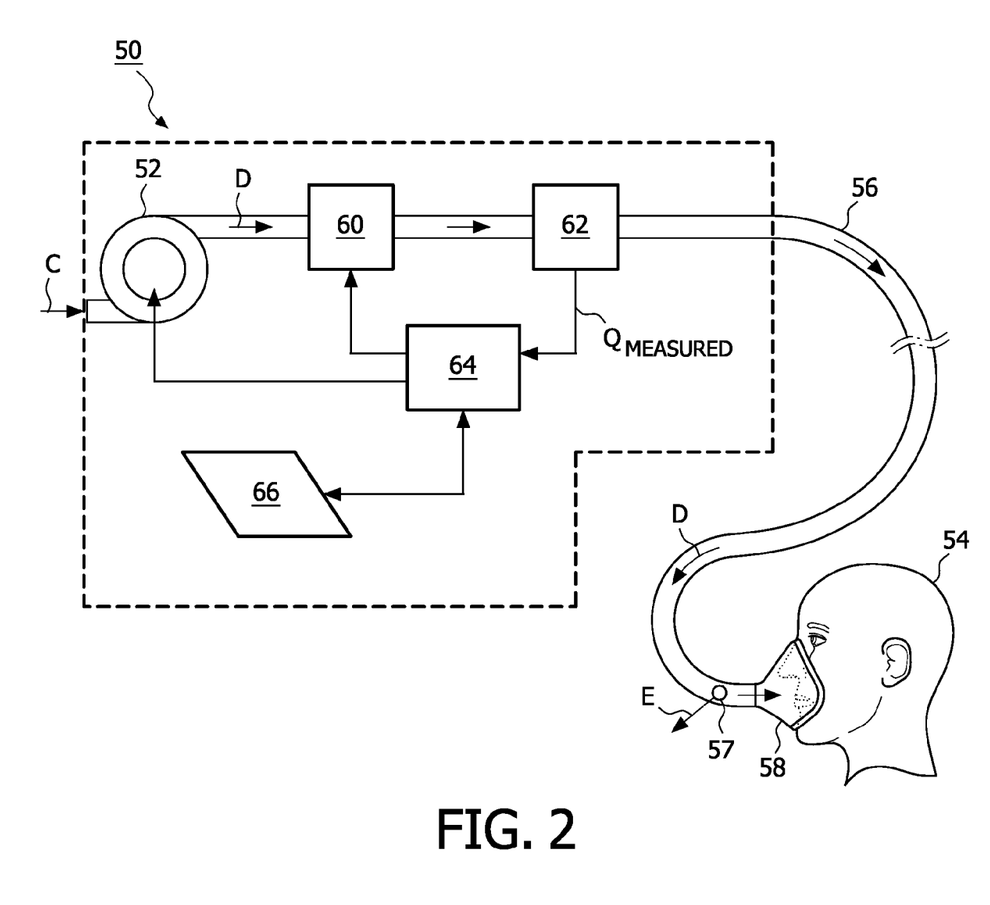
FIG. 2 is a pressure support system according to one, non-limiting embodiment of the invention.

As noted above, in the preferred embodiments, the positive pressure support that is provided to the patient is bi-level positive pressure support. Thus, for ease of illustration and explanation, the particular embodiments described below (FIGS. 2 through 7) will employ such bi-level positive pressure support. It is to be understood, however, that that is not meant to be limiting, and that other forms of positive pressure support (i.e., other therapeutic waveforms where the pressure delivered to the user is above atmospheric pressure) provided during at least part of the inspiratory phase and possibly also during the at least part of the expiratory phase of the patient are also contemplated. FIG. 2 is a schematic diagram of a pressure support system 50 according to one particular, non-limiting embodiment that may be adapted to provide bi-level positive pressure support therapy for treating lung disease, such as asthma or COPD, as described herein. Referring to FIG. 2, the pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. The gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. The pressurized flow of breathing gas, generally indicated by arrow D from the gas flow generator 52, is delivered via a delivery conduit 56 to a breathing mask or patient interface 58 of any known construction, which is typically worn by or otherwise attached to the patient 54 during therapy to communicate the flow of breathing gas to the airway of the patient. The delivery conduit 56 and the patient interface device 58 are typically collectively referred to as a patient circuit.

The pressure support system 50 shown in FIG. 2 is what is known as a single-limb system, meaning that the patient circuit includes only a delivery conduit 56 connecting the patient 54 to the pressure support system 50. As such, an exhaust vent 57 is provided in the delivery conduit 56 for venting exhaled gasses from the system as indicated by arrow E. It should be noted that the exhaust vent 57 can be provided at other locations in addition to or instead of in the delivery conduit 56, such as in the patient interface device 58. It should also be understood that the exhaust vent 57 can have a wide variety of configurations depending on the desired manner in which gas is to be vented from the pressure support system 50.

The present invention also contemplates that the pressure support system 50 can be a two-limb system, having a delivery conduit and an exhaust conduit connected to the patient 54. In a two-limb system, the exhaust conduit carries exhaust gas from the patient 54 and includes an exhaust valve at the end distal from the patient 54. The exhaust valve in such an embodiment is typically actively controlled to maintain a desired level or pressure in the system, which is commonly known as positive end expiratory pressure (PEEP).

Furthermore, in the illustrated exemplary embodiment of the pressure support system 50 shown in FIG. 2, the patient interface 58 is a nasal mask. It is to be understood, however, that the patient interface 58 can include a nasal/oral mask, nasal pillows, or any other device that provides a suitable gas flow communicating function. Also, for purposes of the present invention, the phrase "patient interface" can include the delivery conduit 56 and any other structures that connect the source of pressurized breathing gas to the patient.

In the illustrated embodiment, the pressure support system 50 includes a pressure controller in the form of a valve 60 provided in the delivery conduit 56. The valve 60 controls the pressure of the flow of breathing gas from the flow generator 52 that is delivered to the patient 54. For present purposes, the flow generator 52 and the valve 60 are collectively referred to as a pressure generating system because they act in concert to control the pressure and/or flow of gas delivered to the patient. However, it should be apparent that other techniques for controlling the pressure of the gas delivered to the patient, such as varying the blower speed of the flow generator 52, either alone or in combination with a pressure control valve, are contemplated by the present invention. Thus, the valve 60 is optional depending on the technique used to control the pressure of the flow of breathing gas delivered to the patient 54. If the valve 60 is eliminated, the pressure generating system corresponds to the flow generator 52 alone, and the pressure of gas in the patient circuit is controlled, for example, by controlling the motor speed of the flow generator 52.

The pressure support system 50 further includes a flow sensor 62 that measures the flow of the breathing gas within the delivery conduit 56. In the particular embodiment shown in FIG. 2, the flow sensor 62 is interposed in line with the delivery conduit 56, most preferably downstream of the valve 60. The flow sensor 62 generates a flow signal $Q_{MEASURED}$ that is provided to a controller 64 and is used by the controller 64 to determine the flow of gas at the patient 54. Of course, other techniques for measuring the respiratory flow of the patient 54 are contemplated by the present invention, such as, without limitation, measuring the flow directly at the patient 54 or at other locations along the delivery conduit 56, measuring patient flow based on the operation of the flow generator 52, and measuring patient flow using a flow sensor upstream of the valve 60. The controller 64 may be, for example, a microprocessor, a microcontroller or some other suitable processing device, that includes or is operatively coupled to a memory (not shown) that provides a storage medium for data and software executable by the controller 64 for controlling the operation of the pressure support system 50, including monitoring characteristics of patient respiration and controlling the flow of breathing gas based thereon as described in greater detail herein. Finally, an input/output device 66 is provided for setting various parameters used by the pressure support system 50, as well as for displaying and outputting information and data to a user, such as a clinician or caregiver.

Figure 3A:
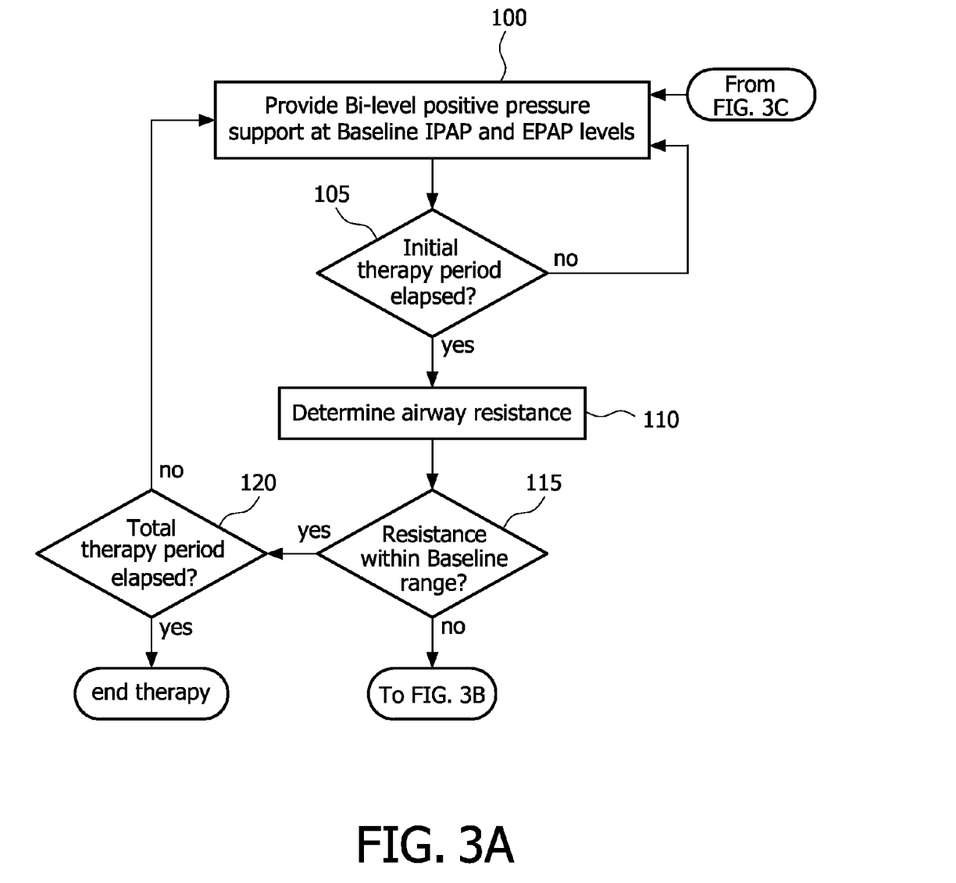
FIGS. 3A, 3B and 3C are a flowchart showing a method of treating asthma according to one particular, non-limiting embodiment of the invention using bi-level positive pressure support therapy.
Figure 3B:
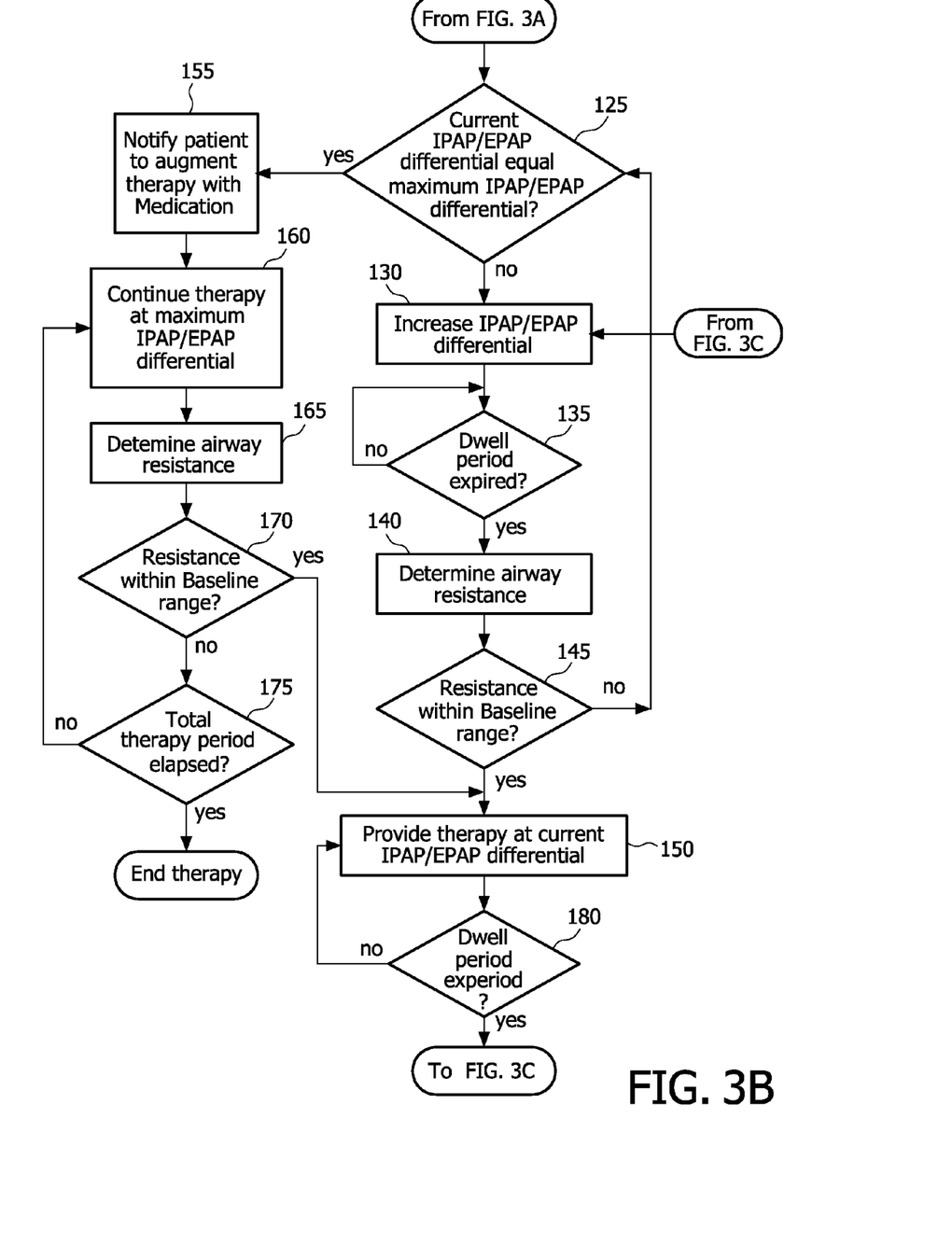
Figure 3C:
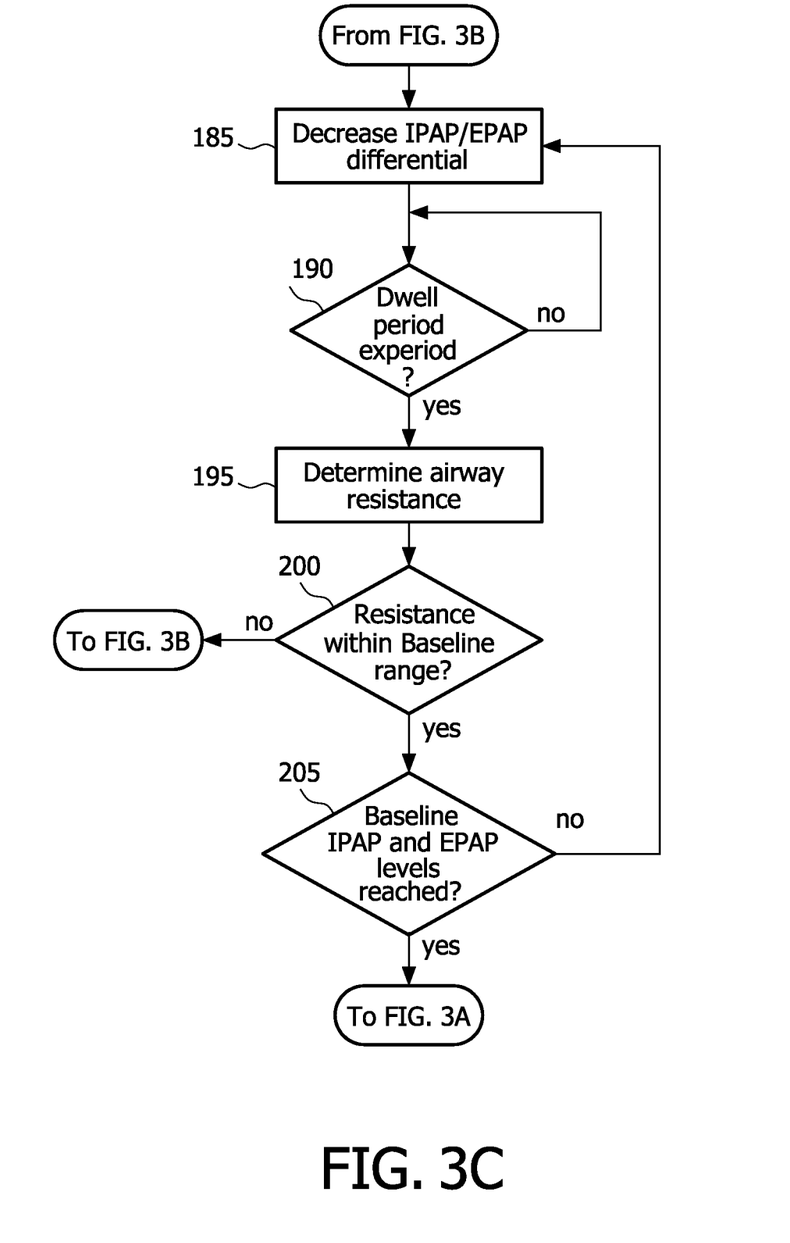

FIGS. 3A, 3B and 3C are a flowchart showing a method of treating lung disease, such as asthma or COPD, according to one particular, non-limiting embodiment of the invention using bi-level positive pressure support therapy. The method shown in FIGS. 3A, 3B and 3C may be implemented in the exemplary pressure support system 50 shown in FIG. 2 (or in another suitable pressure support system). For illustrative purposes, the method will be described herein as implemented in the pressure support system 50. In the method shown in FIGS. 3A, 3B and 3C, lung disease, such as asthma or COPD, therapy is provided by determining a parameter indicative of the patient's pulmonary mechanics, and then determining and varying the bi-level positive pressure support therapy settings (e.g., without limitation, the IPAP/EPAP differential $\Delta P$) based on the determined parameter. In the particular embodiment shown in FIGS. 3A, 3B and 3C, the parameter indicative of the patient's pulmonary mechanics that is used is the patient's upper airway resistance. It is to be understood that that is merely the preferred parameter that may be used, and is not meant to be limiting. Other suitable parameters that may be determined by the pressure support system 50 such as, without limitation, lung compliance, may also be employed.

A number of different suitable methods for determining upper airway resistance and/or lung compliance using the pressure support system 50 are possible. Such methods include methods based on a measured flow signal (e.g., $Q_{MEASURED}$ in FIG. 2). However, as is known, one of the most challenging problems in the non-invasive estimation of upper airway resistance and/or lung compliance relates to how to eliminate the effects of the diaphragmatic muscle pressure ($P_{mus}$) on the measured flow signal, since the $P_{mus}$ component in the flow signal typically leads to large estimation errors.

The assignee of the present invention has developed a flow signal-based method for the non-invasive estimation of upper airway resistance and/or lung compliance that is based on the single compartment lung model and that resolves the issue of the $P_{mus}$ component using bi-level therapy. Specifically, two different IPAP pressures (e.g., 2 cmH$_2$O apart) are applied on successive breaths, and the flow responses are measured and then subtracted from one another. Subtracting the flow responses removes the flow component caused by the diaphragm (i.e., the $P_{mus}$ component), leaving a signal that is the result of the pressure difference applied by the external source. A least squares error fit of the data may then be used to determine the upper airway resistance and lung compliance. Specifically, using least squares linear regression analysis of the natural logarithm of the exponential flow response of a single compartment model to the external pressure source, intercept and slope can be determined. From these values, the time constant and lung compliance can be determined, which then allows the upper airway resistance to be determined.

The assignee of the present invention has also developed a similar, yet slightly different, method for estimating lung compliance and airway resistance by using the first-order single-compartment lung model equations and a randomized pattern of varying the pressure support (pressure support is the difference between the pressure applied during inspiration and expiration). This alternate method resolves the issue of the $P_{mus}$ component by taking the difference of the volume response of the system for two different inspiratory pressure settings on successive breaths. With this technique, the lung compliance and $P_{mus}$ can be simply estimated using the steady-state response of the differential volume signal, or approximating this steady state value through numerical methods. An estimation of the airway resistance can follow by using the time response information in the differential volume signal and compliance estimate.

While the particular methods for determining lung compliance and/or airway resistance just described are believed to be particularly applicable to the invention as described herein, a number of other methods for determining upper airway resistance and/or lung compliance are known in the art and may also be utilized in the present invention. For example, United States Patent Application Publication No. 2004/097821, entitled "Method and Breathing Apparatus for Assessing Pulmonary Stress," describes a method for determining lung resistance and compliance that utilizes a single compartment model. In particular, an equation that relates pressure and flow of the single compartment model is directly used to determine resistance and compliance. These values are then used to determine a stress index value that represents the pulmonary stress existing in the respiratory system. U.S. Pat. No. 6,257,234, entitled "Apparatus and Method for Determining Respiratory Mechanics of a Patient and for Controlling a Ventilator Based Thereon", describes a method for non-invasively detecting the resistance and elastance of the patient's respiratory system using forced single pressure oscillation in a range of 3-10 Hz and 2-10 cmH$_2$O. Resistance is detected by controlling the ventilator to superimpose at least one forced single pressure oscillation on the therapeutic pressure and then observing the pressure-flow relation. Elastance is detected by controlling the ventilator to supply a pressure which has the affect of temporarily occluding the respiratory system, waiting until the respiratory system has reached equilibrium, and evaluating the pressure-volume relation. The resistance in elastance parameters are calculated using two or more data points from the pressure, flow and volume signals. U.S. Pat. No. 5,881,724, entitled "Method and Device for Controlling a Respirator for Therapeutic Treatment of Sleep Apnea", describes a method where an individual's respiratory resistance is determined based on the measured pressure amplitude by oscilloresistometry. Specifically, sine wave flow is superimposed onto the respiratory flow and the resultant pressure oscillation is used to determine resistance. U.S. Pat. No. 6,837,242, entitled "Method and Apparatus for Determining Respiratory System Resistance During Assisted Ventilation", describes a method wherein resistance is calculated using a known value of compliance and a measured pressure, volume and flow. Specifically, resistance is measured by finding the pressure-flow relationship through the introduction of perturbations in pressure, flow and volume. $P_{mus}$ is estimated using the total pressure, volume and flow.

Referring to FIGS. 3A, 3B and 3C, the method shown therein will now be described. As described in greater detail below, that method assumes that a baseline upper airway resistance range which represents a normal, non-diseased (e.g., non-asthmatic) condition, has been established. That baseline resistance range may be, for example, preset by a clinician or established by the pressure support system by taking a number of resistance measurements during a time when the patient is not suffering from disease (e.g., asthmatic) symptoms. In addition, the method shown in FIGS. 3A, 3B and 3C also assumes that a baseline level of bi-level positive pressure support at baseline IPAP and EPAP levels has been established, preferably by being input into the pressure support system 50 by a clinician. Thus, the baseline bi-level positive pressure support will have a baseline IPAP/EPAP differential, ΔP, as shown, for example, in FIG. 1. As described in greater detail below, the actual bi-level positive pressure support that is provided to the patient during therapy according to the present method will be varied around and as compared to this baseline therapy based upon the particular airway resistance measurements that are made.

Referring to FIG. 3A, the method begins at step 100, wherein the patient 54 attaches the patient interface 58 in the required manner and bi-level positive pressure support at the baseline IPAP and EPAP levels is provided by the pressure support system 50. The particular embodiment of the method shown in FIGS. 3A, 3B and 3C will provide this baseline level of support for an initial therapy period before the resistance measurements are made and the level of support is varied. Thus, at step 105, a determination is made as to whether the initial therapy period has elapsed. Such initial therapy period may be, for example, five to ten minutes. If the answer at step 105 is no, the method returns to step 100. If, however, the answer at step 105 is yes, meaning that the initial therapy period has elapsed, then, at step 110, the pressure support system 50 determines the airway resistance of the patient 54 using, for example and without limitation, one of the methods described elsewhere herein. Next, at step 115, a determination is made as to whether the measured airway resistance is within the pre-established baseline range. If the answer is yes, then, at step 120, a determination is made as to whether a preset total therapy period has elapsed. That preset total therapy period is the total period over which the therapy of the present invention is to be provided in the current therapy session. If the answer at step 120 is yes, then the therapy is ended and the bi-level positive pressure support is no longer provided by the pressure support system 50. If, however, the answer at step 120 is no, then the method returns to step 100.

As seen in FIG. 3A, if the answer at step 115 is no, meaning that the determined airway resistance is not within the pre-established normal baseline range, then the method proceeds to step 1215 shown in FIG. 3B. As described in greater detail below, the method embodiment shown in FIGS. 3A, 3B and 3C is able to increase the IPAP/EPAP differential up to some preset maximum level. Thus, at step 125, a determination is made as to whether the current IPAP/EPAP differential is equal to the preset maximum IPAP/EPAP differential (i.e., has the maximum IPAP/EPAP differential been reached). If the answer at step 125 is no, then, at step 130, the IPAP/EPAP differential is increased by a predetermined amount. For example, this may be done by both increasing the IPAP level and decreasing the EPAP level, by only increasing the IPAP level or by only decreasing the EPAP level. The amount of the increase is a predetermined step amount that is preferably set by a clinician using the input/output device 66 of the pressure support system 50. In the embodiment shown in FIGS. 3A, 3B and 3C, each time the IPAP/EPAP differential is increased, the therapy will be allowed to dwell for a predetermined dwell period. That predetermined dwell period may be, for example and without limitation, one or more breathing cycles of the patient. Thus, at step 135, a determination is made as to whether the predetermined dwell period has expired. If the answer is no, then the method returns to step 135. If, however, the answer is yes, then, at step 140, the airway resistance is again determined, preferably according to one of the methods described herein. Next, at step 145, a determination is made as to whether the determined airway resistance is within the predetermined baseline range. If the answer at step 145 is no, then, the method returns to step 125. If, however, the answer at step 145 is yes, then the method proceeds to step 150, which is described in greater detail below.

Referring again to step 125, if the answer is yes, meaning that the current IPAP/EPAP differential equals the maximum IPAP/EPAP differential, the method proceeds to step 155. At step 155, the patient is notified to augment the therapy being provided with their medication (e.g., asthma medication). For example, the patient 54 may temporarily remove the patient interface 58 and administer a rescue medication. After the medication is delivered, the patient 54 reattaches the patient interface 58. Alternatively, a medication delivery device such as a nebulizer may be coupled to the patient interface 58 as described in, for example and without limitation, U.S. Pat. No. 5,297,543, entitled "Medication Inhaler Mixer", and United States Patent Application Publication No. 2006/0201500, entitled "Nebulizer Drug Delivery Device for Ventilator", both owned by the assignee hereof, the disclosures of which are incorporated herein by reference. In such an embodiment, at step 155, the pressure support system 50 will automatically cause the medication delivery device to deliver a medication to the patient 54 as therapy is continued. Next, following step 155 (regardless of implementation), the method proceeds to step 160, wherein bi-level positive pressure support therapy at the maximum IPAP/EPAP differential is continued for a predetermined period of time. Thereafter, at step 165, the airway resistance is again determined Then, at step 170, a determination is made as to whether the determined resistance is within the predetermined baseline range. If the answer is no, then, at step 175, a determination is made as to whether the total therapy period has elapsed. If the answer is yes, then therapy is ended. If, however, the answer is no, then the method returns to step 160. If, however, the answer at step 170 is yes, meaning that the determined airway resistance is within the baseline range, then the method proceeds to step 150.

At step 150, which may be reached as a result of either a positive answer at step 145 or a positive answer at step 170 (both meaning that the current determined resistance is within the baseline range), the bi-level positive pressure support therapy is provided at the then current IPAP/EPAP differential. Furthermore, that level of therapy will be provided for a predetermined dwell period. Thus, at step 180, a determination is made as to whether the dwell period has expired. If the answer is no, then the method returns to step 150, wherein therapy is continued. If, however, the answer at step 180 is yes, meaning that the dwell period has expired, then the method proceeds to step 185 in FIG. 3C.

At step 185, the IPAP/EPAP differential is decreased by a predetermined step amount. This step is, in effect, the opposite of step 130 and will preferably be performed in an opposite manner, meaning that depending on the particular implementation used for the increase (described above) the IPAP level may be decreased and the EPAP level may be increased, only the IPAP may be decreased, or only the EPAP level may be increased, in order to achieve the predetermined step decrease. Next, at step 190, a determination is made as to whether the predetermined dwell period has expired. If the answer is no, then the method returns to step 190 in effect creating a loop that awaits the expiration of the dwell period. If, however, the answer at step 190 is yes, meaning that the dwell period has expired, then, at step 195, the airway resistance of the patient 54 is determined as described elsewhere herein. At step 200, a determination is made as to whether the resistance that is determined is within the predetermined baseline range. If the answer at step 200 is no, then the method returns to step 130 of FIG. 3B and the IPAP/EPAP differential is increased as described previously. If, however, the answer at step 200 is yes, then, at step 205, a determination is made as to whether the baseline IPAP and EPAP levels have been reached. If the answer at step 205 is no, then the method returns to step 185, and the IPAP/EPAP differential is further decreased by a predetermined step as described. If the answer at step 205 is yes, meaning that the baseline level of therapy has been reached, then the method returns to step 100 of FIG. 3A and processing continues as described previously.

Thus, in short, according to an aspect of the present invention, and as shown in the particular exemplary embodiment of FIGS. 3A, 3B and 3C, as airway resistance measurements indicate an increase in airway resistance as compared to a baseline (which increase indicates a worsening of the systems of the patient 54), the IPAP/EPAP differential will be increased at predetermined increments or magnitudes. The IPAP/EPAP differential will continue to be increased until the airway resistance of the patient improves, or until the predetermined maximum IPAP/EPAP differential is reached. If the maximum IPAP/EPAP differential is reached without the desired improvement in the airway resistance of the patient 54, then the patient 54 is notified to augment the bi-level positive pressure support therapy with their medication (e.g., asthma medication) (alternatively, the medication may be administered automatically as described herein by an integrated delivery device). If the airway resistance of the patient 54 is able to be improved with the increased IPAP/EPAP differential, then the therapy will dwell at that setting for a predetermined duration of time, and thereafter the IPAP/EPAP differential will be decreased in a step-wise fashion. If the airway resistance of the patient remains normal as the IPAP/EPAP differential is decreased, it will be decreased until the baseline level is reached. Otherwise, if during the IPAP/EPAP differential reduction the airway resistance moves away from normal, then the IPAP/EPAP differential is again increased in effort to reestablish the normal airway resistance.

Figure 4:
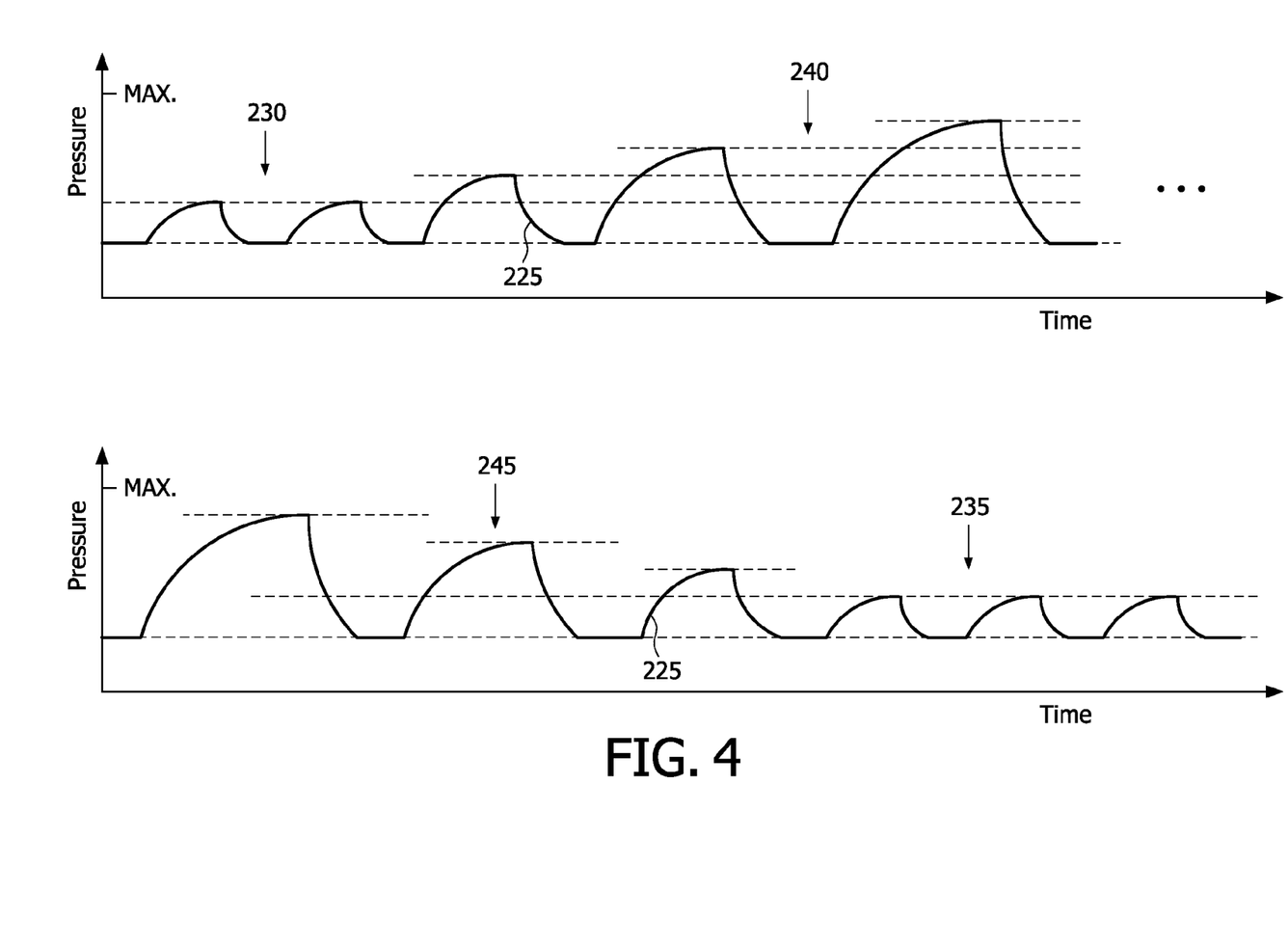
FIG. 4 is an exemplary pressure curve that may result from the method of FIGS. 3A, 3B and 3C.

FIG. 4 shows an exemplary pressure curve 255 that may provide bi-level positive pressure support therapy to the patient 54 according to the method shown in FIGS. 3A, 3B and 3C. As seen in FIG. 4, the pressure curve 225 includes sections 230 and 235 where the baseline bi-level positive pressure support therapy is provided, a section 240 wherein the IPAP/EPAP differential is increased, and a section 245 wherein the IPAP/EPAP differential is decreased. For illustrative purposes, sections of the pressure curve 225 that may include variations resulting from one or more methods of determining airway resistance are omitted. Furthermore, it will be appreciated that the pressure curve 225 is but one exemplary possibility that may result from the method shown in FIGS. 3A, 3B and 3C, and that many other variations are possible.

Furthermore, in the particular embodiment shown in FIGS. 3A, 3B and 3C, the parameter indicative of the patient's pulmonary mechanics that is employed is upper airway resistance. It should be understood, however, that that is not meant to be limiting, and that instead other such parameters, including, without limitation, lung compliance, may also be employed without departing from the scope of the present invention.

In addition, in the particular embodiment shown in FIGS. 3A, 3B and 3C, the parameter indicative of the patient's pulmonary mechanics is determined in a separate step from the resulting therapy (which preferably has a fixed duration). This, however, does have to be the case. Instead, the parameter indicative of the patient's pulmonary mechanics (e.g., resistance or lung compliance) can be determined during therapy, and the pressures can be modified/titrated simultaneously, in real time.

Furthermore, in the particular embodiment shown in FIGS. 2, 3A, 3B and 3C, the parameter indicative of the patient's pulmonary mechanics is determined by the pressure support system 50. This is merely one particular embodiment. Alternately, the determination of the parameter indicative of the patient's pulmonary mechanics could be accomplished by a separate (external to the pressure support system 50) device and transmitted, wired or wirelessly, to the pressure support system 50. For example, a hand-held (portable) spirometer, which is a device used by asthma patients to determine effectiveness of therapy, could be employed to determine the parameter indicative of the patient's pulmonary mechanics and automatically transmit the determined data to the pressure support system 50 through an appropriate interface provided as a part thereof for use in the methods as described elsewhere herein. As a further alternative, the data determined by the separate device such as a spirometer can be manually input (as opposed to automatically transmitted) into the pressure support system 50 using a suitable user interface such as a keypad or touchscreen for use in the methods as described elsewhere herein.

In still another particular embodiment, a device like a modem, memory card, or other data connectivity method, could be used to send data to the patient's care provider relating to compliance and effectiveness of therapy for a predetermined time period (e.g., respiratory resistance or lung compliance over one or more days). In addition, in another particular embodiment, the pressure support system 50 can have a feedback component that indicates to the user how well they are stretching their lungs. For example, an "effectiveness of therapy" feedback component could be displayed numerically and/or graphically on a display provided as part of the pressure support system 50, and/or provided in the form of auditory feedback using a feedback device such as a speaker provided as part of the pressure support system 50. One method of feedback could indicate increasing (or decreasing) tidal volume of the user resulting from the therapy over a predetermined period of time, or meeting or exceeding a target tidal volume. As known in the art, tidal volume can be determined by integrating airflow through portions of the respiratory cycle.

Figure 5:
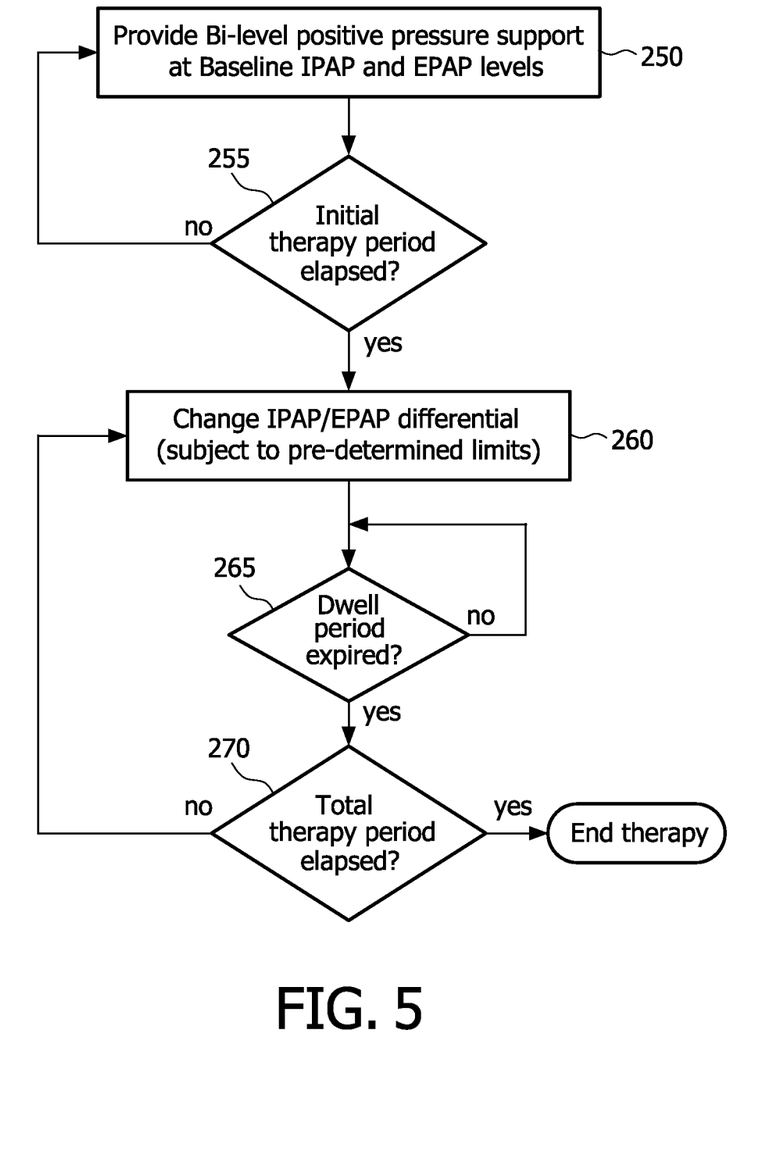
FIG. 5 is a flowchart showing a method of treating asthma according to an alternative embodiment of the invention using bi-level positive pressure support therapy.

FIG. 5 is a flowchart showing a method of treating asthma according to an alternative embodiment of the invention using bi-level positive pressure support therapy. The method of FIG. 5 may be implemented in the exemplary pressure support system 50 shown in FIG. 2 (or in another suitable pressure support system). In the method shown in FIG. 5, asthma therapy is provided by periodically changing the IPAP/EPAP differential that is provided to the patient 54 as compared to a baseline level. In other words, the range of the IPAP and EPAP settings are, in this embodiment, varied to dynamically manipulate the muscles of the patient's upper airway. Preferably, the particular IPAP and EPAP settings, (i.e., the particular IPAP/EPAP differentials), are determined and set pseudo-randomly. Alternatively, the particular IPAP and EPAP settings may be varied according to some predetermined scheme (e.g., a preset pattern) that provides a suitable dynamic manipulation of the muscles of the patient's upper airway.

Referring to FIG. 5, the method begins at step 250, wherein bi-level positive pressure support is provided to the patient by the pressure support system 50 at a predetermined baseline level (i.e., at predetermined baseline IPAP and EPAP levels). Preferably, that baseline level is established by a clinician using the input/output device 66 of the pressure support system 50. In the embodiment shown in FIG. 5, that baseline bi-level positive pressure support therapy is provided for a predetermined initial therapy period which also is preferably established by a clinician using the input/output device 66 of the pressure support system 50. Thus, at step 255, a determination is made as to whether that initial therapy period has elapsed. If the answer is no, then the method returns to step 250, and baseline therapy is continued. If, however, the answer at step 255 is yes, then, at step 260, the IPAP/EPAP differential is changed, either pseudorandomly (within certain predetermined safe limit values) or according to a predetermined scheme that is stored by the controller 64. In the embodiment shown in FIG. 5, the new bi-level positive pressure support therapy at the new IPAP/EPAP differential is provided for a particular dwell period. Thus, following step 260, the method proceeds to step 265, wherein a determination is made as to whether the dwell period has expired. If the answer at step 265 is no, then the method returns to step 265. If, however, the answer at step 265 is yes, meaning that the dwell period has expired, then the method proceeds to step 270, wherein a determination is made as to whether a predetermined total therapy period has elapsed. Preferably, that predetermined total therapy period, which indicates the total time for which the therapy of FIG. 5 is to be provided, is established by a clinician and/or the patient 54 using the input/output device 66 of the pressure support system 50. If the answer at step 270 is no, meaning that therapy is to continue, then the method returns to step 260, where the IPAP/EPAP differential is again changed. If the answer at step 270 is yes, meaning that the total therapy period has elapsed, then therapy ends. Thus, the method of FIG. 5 will, following an initial period of baseline therapy, result in bi-level positive pressure support therapy with periodically varying IPAP and EPAP settings being provided to the patient 54 until a predetermined therapy period has elapsed.

The dwell period of step 265 may, for example, be equal to the length of one breathing cycle of the patient 54, in which case the IPAP/EPAP differential will change breath-to-breath, or, alternatively, may encompass multiple breathing cycles of the patient 54, in which case the IPAP/EPAP differential will remain the same for a number of breathing cycles and then change to a new level for a number of breathing cycles, and so on.

Figure 6:
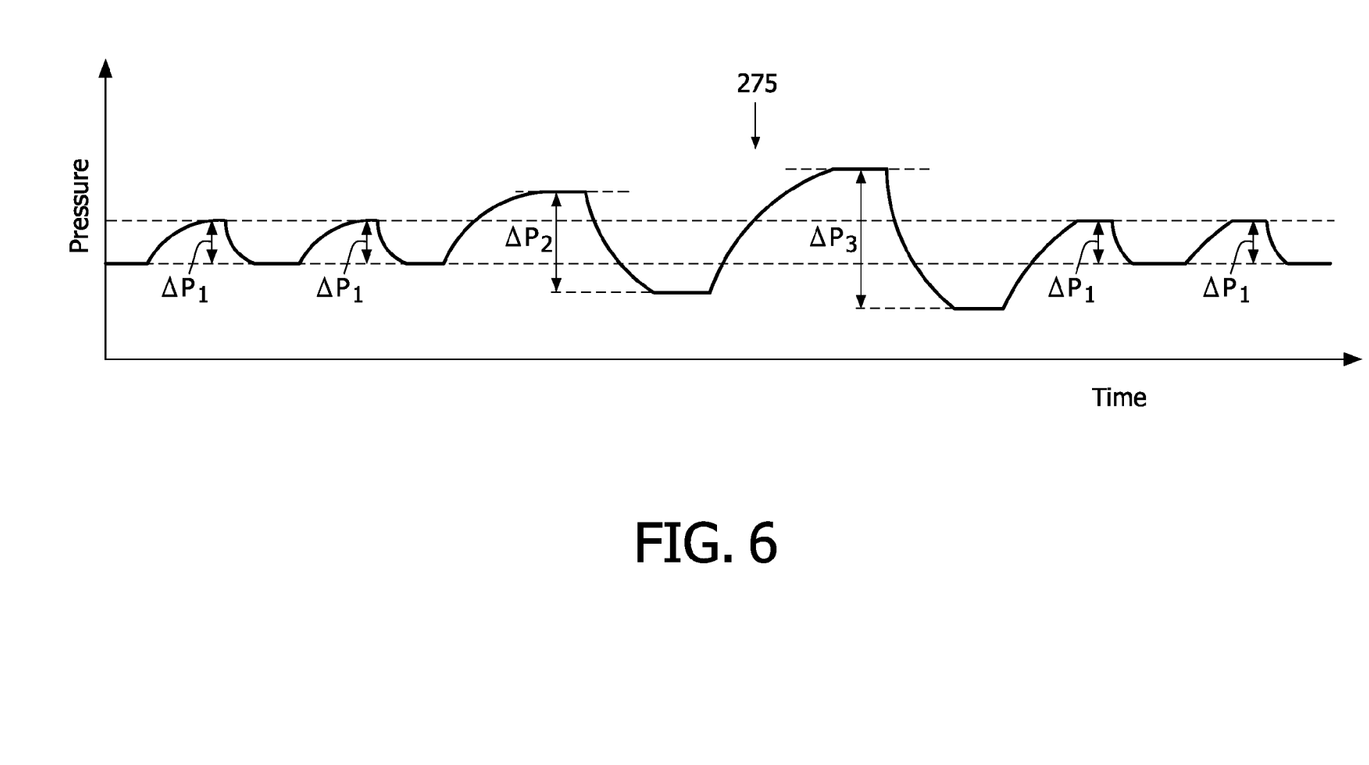
FIGS. 6 and 7 show exemplary pressure curves that may result from the method of FIG. 5.
Figure 7:
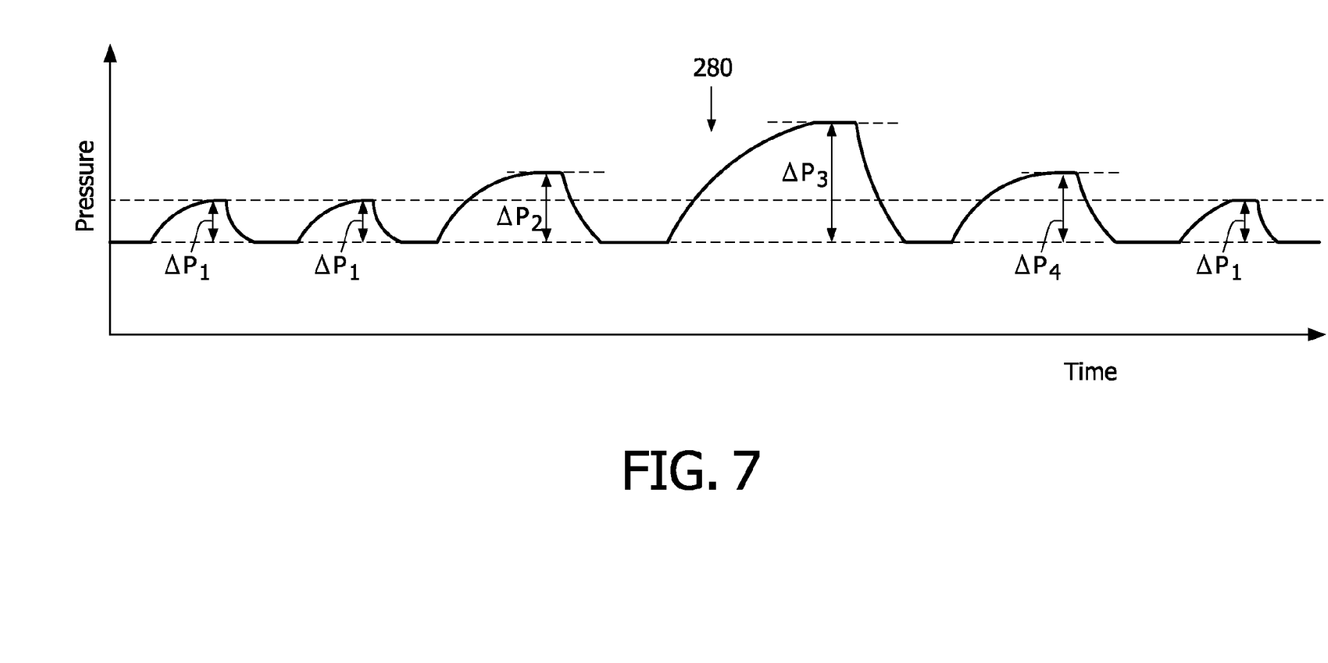

FIGS. 6 and 7 show exemplary pressure curves 275 and 280, respectively, which may result from the method shown in FIG. 5. As seen in FIGS. 6 and 7, the pressure curves 275 and 280 include baseline IPAP/EPAP differentials, indicated by $\Delta P_1$, and varying IPAP/EPAP differentials, indicated by $\Delta P_2$, $\Delta P_3$ and, in the case of pressure curve 280, $\Delta P_4$. Again, the pressure curves 275 and 280 shown in FIGS. 6 and 7, respectively, are meant to be exemplary only and are not meant to be limiting. Thus, other pressure curves having IPAP/EPAP differentials that vary in other ways may also result from the method shown in FIG. 5 and thus are within the scope of the present invention.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. For example, the embodiments disclosed elsewhere herein have been described in connection with the treatment of asthma. However, the methods and system described herein may be employed to treat other lung diseases that effect the airways, such as, without limitation, chronic obstructive pulmonary disease (COPD). Accordingly, the invention is not to be considered as limited by the foregoing description but is only limited by the scope of the appended claims.

What is claimed is:

1. A method of treating lung disease, comprising:
    delivering positive pressure support to an airway of a patient during a plurality of respiratory cycles that include inhalation phases and exhalation phases, wherein the positive pressure support includes an inspiratory positive airway pressure (IPAP) level and an expiratory positive airway pressure (EPAP) level, wherein the IPAP level is higher than the EPAP level by a pressure differential, wherein the delivery is timed by detecting onsets of the inhalation phases and the exhalation phases;
    increasing the pressure differential between the IPAP level and the EPAP level for multiple respiratory cycles; and
    decreasing the pressure differential between the IPAP level and the EPAP level for multiple respiratory cycles, subsequent to the increasing,
    wherein the increasing and the decreasing are performed regardless of respiratory activity during the plurality of respiratory cycles.

2. The method according to claim 1, further comprising:
    determining a respiratory parameter that is indicative of pulmonary mechanics of the patient; and
    determining whether the respiratory parameter breaches a threshold value,
    wherein both increasing and decreasing the pressure differential between the IPAP level and the EPAP level are performed responsive to a determination that the respiratory parameter breaches the threshold value.

3. The method according to claim 2, wherein the respiratory parameter is based on upper airway resistance.

4. The method according to claim 2, wherein the respiratory parameter is based on lung compliance.

5. The method according to claim 1, wherein increasing and decreasing the pressure differential are performed by increasing and decreasing the (IPAP) level corresponding.

6. The method according to claim 1, wherein increasing the pressure differential is performed by increasing the IPAP level and decreasing the EPAP level, and wherein decreasing the pressure differential is preformed by decreasing the IPAP level and increasing the EPAP level.

7. The method according to claim 1, wherein increasing the pressure differential is independent form flow rates during the plurality of respiratory cycles.

8. The method according to claim 1, wherein the lung disease is asthma.

9. The method according to claim 1, wherein the lung disease is COPD.

10. A pressure support system for treating lung disease, comprising:
    a pressure generating system;
    a sensor configured to generate output signals conveying information related to one or more respiratory parameters;
    a patient circuit operatively coupled to the pressure generating system; and
    a controller operatively coupled to the pressure generating system, the controller being adapted to:
        control the pressure generating system to deliver positive pressure support to an airway of a patient through the patient circuit during a plurality of respiratory cycles that include inhalation phases and exhalation phases, wherein the positive pressure support an inspiratory positive airway pressure (IPAP) level and an expiratory positive airway pressure (EPAP) level, wherein the IPAP level is higher than the EPAP level by a pressure differential, wherein the delivery is timed by detecting onsets of the inhalation phases and the exhalation phases based on the generated output signals,
        increase the pressure differential between the IPAP level and the EPAP level for multiple respiratory cycles, and
        decrease the pressure differential between the IPAP level and the EPAP level for multiple respiratory cycles, subsequent to the increasing,
    wherein the increasing and the decreasing are performed regardless of respiratory activity during the plurality of respiratory cycles.

11. The system according to claim 10, wherein the controller is further adapted to:
    determine a respiratory parameter that is indicative of pulmonary mechanics of the patient, and
    determine whether the respiratory parameter breaches a threshold value,
    wherein both increasing and decreasing the pressure differential between the IPAP level and the EPAP level are performed responsive to a determination that the respiratory parameter breaches the threshold value.

12. The system according to claim 11, wherein the respiratory parameter is based on upper airway resistance.

13. The system according to claim 11, wherein the respiratory parameter is based on lung compliance.

14. The system according to claim 10, wherein the controller is adapted to increase and decrease the pressure differential by increasing and decreasing the IPAP level correspondingly.

15. The system according to claim 10, wherein the controller is adapted to increase the pressure differential by increasing the IPAP level and decreasing the EPAP level, and wherein the controller is adapter to decrease the pressure differential by decreasing the IPAP level and increasing the EPAP level.

16. The system according to claim 10, wherein the controller is adapted to increase the pressure differential independently from generated output signals during the plurality of respiratory cycles.

17. The system according to claim 10, wherein the ling disease is asthma.

18. The system according to claim 10, wherein the lung disease is COPD.

* * * * *